United States Patent [19]

Dawidson et al.

[11] 4,254,115

[45] Mar. 3, 1981

[54] PHOSPHOLIPID DERIVATIVE WITH AN ANTILIPEMIC AND ANTIARTERIOSCLEROTIC EFFECT

[75] Inventors: Herbert Dawidson, Königsdorf; Hans Betzing, Horrem, both of Fed. Rep. of Germany

[73] Assignee: A. Nattermann & Cie. GmbH, Cologne, Fed. Rep. of Germany

[21] Appl. No.: 49,064

[22] Filed: Jun. 18, 1979

[51] Int. Cl.$^3$ .......................... A61K 31/16; C07F 9/10
[52] U.S. Cl. ..................................... 424/211; 260/403
[58] Field of Search .......................... 260/403; 424/211

[56] References Cited

U.S. PATENT DOCUMENTS 2,791,594   5/1957   Hennessy et al. ..................... 260/403

FOREIGN PATENT DOCUMENTS 2756866   6/1979   Fed. Rep. of Germany ........... 260/403

OTHER PUBLICATIONS

Wagner et al., "Synthetic Organic Chemistry", (1953), pp. 566–567.
Ansel et al., "Phospholipids", vol. 3, 1964, pp. 34–35.
Harwood, "Photochemistry", vol. 15, 1976, pp. 1459–1463.
Hasegawa et al., "Lipids", vol. 8, 1973, pp. 631–634.
Wittcoff, "Phosphatides", 1951, pp. 222–223, 231–232.

*Primary Examiner*—Anton H. Sutto
*Attorney, Agent, or Firm*—Burns, Doane, Swecker & Mathis

[57] ABSTRACT

Novel n-oleyl derivatives of natural and synthetic phosphatidyl ethanolamines are provided. Such derivatives exhibit antilipemic and antiarteriosclerotic properties and are thus useful in pharmaceutical preparations.

2 Claims, No Drawings

PHOSPHOLIPID DERIVATIVE WITH AN ANTILIPEMIC AND ANTIARTERIOSCLEROTIC EFFECT

DESCRIPTION OF THE INVENTION

Naturally occurring phospholipids which can be produced either from egg yoke, soya beans, rape, peanuts or sunflowers, consist of a mixture of chemically different phospholipids with phosphatidylcholine, phosphatidylethanolamine and phosphatidylinositide being the predominant components. It has been known for some time that phosphatidcholine, or phosphatidylcholine-enriched phospholipid fractions together with unsaturated aliphatic acids, mainly in multiples, possess an advantageous metabolic effect on the symptoms of diseases such as arteriosclerosis, hyperlipemias and diabetes. However, such an effect has been known heretofore only in the case of choline-containing glycerinephospholipids. The phosphatidylethanolamine, on the other hand, does not display any antiarteriosclerotic or antilipemic effects. Phosphatidylethanolamine, however, is a component of the phosphatides and can cause undesirable side effects if phospholipids are administered. It is known that the primary amino group of this phosphatide can be acylated by reaction with polycarboxylic-acid-anhydrides (see German Pat. No. 721 002) in order to improve its solubility characteristics. The acylation of lecithin-containing mixtures is known as described in U.S. Pat. No. 2,791,594, and the acylation of the phosphatides with acetic acid anhydrides has been disclosed by British Pat. Nos. 766 394 and 974 432 as well as by the published German Patent Application No. 15 43 937. Higher n-aliphatic-acid-acyl compounds of phosphatidylethanolamine were detected in small quantities in nautrally occurring glycerinephospholipids and especially in the phospholipid mixture of the soya beans. Specifically n-acylphosphatidylethanolamine was admixed with different aliphatic acids where the palmitic acid is quantitatively predominant at approximately 65% of the mixture.

It has been found surprisingly and unexpectedly found that phosphatidylethanolamines of natural as well as synthetic origin can be converted by acylation with oleic acid to new n-oleylphosphatidylethanolamines which demonstrate, even at small dosages, a pronounced antiarteriosclerotic, or antilipemic effect in animal tests. It is surprising and unexpected that this effect can be clearly detected only in the case of oleic acid derivatives of the phosphatidylethanolamines and is not observed in the case of corresponding compounds which are derived either from the highly unsaturated aliphatic acids or from the saturated aliphatic acids with widely differing chain lengths. Even the n-linolate of the phosphatidylethanolamine only exhibits a moderate antilipemic effect even though n-linolyl compounds of cyclic amines, such as the cyclohexyllinolamide, have been known for a long time specifically for their lipid-reducing effect. Therefore, it has definitely not been obvious, and it could not be foreseen by a person skilled in the art to prepare the n-oleylphosphatidylethanolamines and to test the same for their antilipemic or respectively antiarteriosclerotic effect.

The n-oleyl derivatives of the present invention may be manufactured by dissolving pure phosphatidylethanolamine or phosphatidylethanolamine-containing phospholipid fractions, such as raw phosphatides or phospholipid fractions which are soluble, or respectively insoluble, in alcohol, in aliphatic, cyclic or chlorinated hydrocarbon, or respectively tetrahydrofuran or dioxan, and after an admixture of basic compounds, such as triethylamine, pyridine or similar acid acceptors, are then caused to react with oleic acid chloride or, by use of the anhydride principle, with oleic acid and formic acid chloride.

The fact that cephalin-containing phosphatide fractions can be used for the n-oleyl production of the phosphatidylethanolamine is economically important. Phospholipid mixtures containing the biologically valuable phosphatidylcholine together with the n-oleylphosphatidylethanolamines of the present invention which have a good antilipemic and antiarteriosclerotic effect when applied orally, can thus be produced in a simple manner.

In order to produce a suitable oral therapeutic form of administration, the n-oleylphosphatidylethanolamines of the present invention can be placed into soft gelatin capsules after the admixture of an antioxidant, such as for example Vitamin E. In the case of the mixture of the n-oleylphosphatidylethanolamines with other phospholipids the admixture can be placed into capsules after the admixture of mono-, di or triglycerides obtained from natural aliphatic acids. A suitable method for oral application in solid form is the adsorbing of the n-oleylphosphatidylethanolamines on Aerosil or various celites, to give some examples. Lactose, calcium carbonate and magnesium stearate can be used as auxiliary materials in the manufacture of solid forms in addition to antioxidants such as tocopherol or ascorbic acid. The pharmaceutical preparations of the present invention may also contain pigments, aromatic substances and preservatives.

The daily dosage of n-oleylphosphatidylethanolamine in a pharmaceutical preparation for oral use can range from 100 to 2000 mg, with this amount normally divided into several smaller doses of 50 to 500 mg, to be given, for example, 2 to 4 times daily.

The examples given below serve to explain the invention in greater detail.

The following tests were employed to determine the therapeutic effect of the n-oleyl derivatives of the present invention:

(a) Prophylactic application

The n-oleyl derivative (i.e., n-oleyl cephalin) was orally administered to the test animals. Twenty-four hours later an intraperitoneal application of triton-WR 1339 (to produce hyperlipemia) occurred. Forty-eight hours after the triton application, serum was analyzed for lipids and compared with a control group. The results are depicted in Table I.

(b) Therapeutic application

Triton-WR 1339 was intraperitoneally administered to the test animals. One hour later the n-oleyl cephalin was orally administered. Forty-eight hours after the triton is administered, serum is analyzed for lipids and evaluated against a control group. The results are depicted in Table I.

(c) Biochemical screening

In accordance with the procedures set forth in Fletcher, M. J., Clin. Chim. Acta., Vol. 22, pages 393 (1968), the n-oleyl cephalin was orally administered to unstressed animals. Four hours later serum was analyzed for lipids and evaluated against a control group. The results are depicted in Table I.

TABLE I

| Test | | N-oleylcephalin | | Clofibrate | |
| --- | --- | --- | --- | --- | --- |
| 1. Acute triton test (1 × prophylactic application) on rats | Total lipids | E.D.$_{50}$ | 0.29 mg/kg BW* | Dosings up to 250 mg/kg BW ineffective | |
| | Phospholipids | " | 0.62 mg/kg BW | | |
| | Triglycerides | " | 0.18 mg/kg BW | Dosing 500 mg/kg BW very effective | |
| | Total cholesterol | Effect from | 0.01 mg/kg BW | | |
| | Free cholesterol | Effect from | 0.10 mg/kg BW | | |
| 2. Acute triton test (1 × therapeutic application) on rats | Total lipids | E.D.$_{50}$ | 8.49 mg/kg BW | Drop from | 250 mg/kg BW |
| | Triglycerides | " | 5.63 mg/kg BW | Drop from | 250 mg/kg BW |
| | Total cholesterol | " | 278.86 mg/kg BW | No effect up to | 500 mg/kg BW |
| | Phospholipids | Drop from | 0.10 mg/kg BW | Drop from | 500 mg/kg BW |
| | Free cholesterol | Drop from | 0.10 mg/kg BW | No effect up to | 500 mg/kg BW |
| 3. Biochemical screening (unstressed rat) | Total lipids | | 50 mg/kg BW | Drop from | 100 mg/kg BW |
| | Phospholipids | | 50 mg/kg BW | Not determined | |
| | Triglycerides | Drop from | 50 mg/kg BW | Drop from | 50 mg/kg BW |
| | Total cholesterol | | 50 mg/kg BW | Drop from | 50 mg/kg BW |
| | Free cholesterol | | 50 mg/kg BW | Not determined | |
| 4. Acute toxicity | LD$_{50}$ mouse | | >4640 mg/kg BW | | 2960 mg/kg BW |
| | LD$_0$ mouse | | >4640 mg/kg BW | | ~1470 mg/kg BW |
| | LD$_{50}$ rat | | >5000 mg/kg BW | | 1100 mg/kg BW |
| | LD$_0$ rat | | >5000 mg/kg BW | | ~681 mg/kg BW |
| 5. Subchronic toxicity | | Rat 4 weeks: Lowest toxic dose between 250 and 1250 mg/kg BW | | Rat 13 weeks: Lowest toxic dose between 88 and 265 mg/kg BW | |

*BW = body weight

The data contained within Table I demonstrates that the n-oleyl derivatives of the present invention have a marked hypolipemic or antihyperlipemic effect, even when administered in a low dosage. On the other hand, a high dosage of clofibrate (150 to 500 times higher) is usually necessary to achieve comparable results. Furthermore, the compounds of the present invention exhibit less acute and sub-acute toxicity.

EXAMPLE 1

100 grams of chemically pure phosphatidylethanolamine, produced by columnchromatographic separation of a soyalecithin fraction of high phosphatidylethanolamine content and insoluble in alcohol by use of silica gel and with chloroform-methanol serving as eluant, are dissolved in 500 ml of toluene and are treated, after an admixture of 38 ml of triethylamine, with a solution of 41.2 gram of oleic acid chloride in 60 ml of toluene under stirring. The stirring is continued for one hour at room temperature and the precipitated triethylaminehydrochloride is then filtered out and the solvent is removed in the vacuum at 60° C. bath temperature and a nitrogen atmosphere. The n-oleyphosphatidylethanolamine remains in the form of viscous oil with a yellow-brown coloring. Yield: 115 gram which corresponds to 96% of the theoretical value. Rf value of the n-oleylphosphatidylethanolamine=0.72 by the use of silica gel "G-Fertigplatten 60 F$_{254}$ (firm of Merck)", eluent chloroform-methanol-12.5% of NH$_4$OH ratio 70:25:5 (v/v/v).

EXAMPLE 2

19.3 grams of oleic acid are dissolved in 300 ml of tetrahydrofuran and are cooled to 0° C. under stirring after the admixture of 9.5 ml of triethylamine. The solution is treated with 6.5 ml of chlorinated formic acid ethyl ester, and after 5 minutes, is then treated with a solution of 50 grams of phosphatidylethanolamine—produced in the manner described in Example 1—in 120 ml of tetrahydrofuran. After an admixture of 9.5 ml of triethylamine, the reaction mixture is stirred for one hour at room temperature, the precipitated triethylaminehydrochloride is filtered out and the solution is evaporated in a vacuum at 60° C. bath temperature. The n-oleylphosphatidylethanolamine remains in the form of a viscous oil with a yellow-brown coloring. Yield: 58 gram which corresponds to 97% of the theoretical value.

EXAMPLE 3

200 grams of a soyaphospatide fraction, soluble in alcohol and produced by the repeated (continuous) extraction of de-oiled raw soya bean phosphatide by the use of ethanol at 40° to 60° C., are dissolved in 800 ml of chloroform and are treated after the admixture of 25 ml of pyridine with a solution of 16.4 grams of oleic acid chloride in 50 ml of chloroform under stirring. The stirring is continued for one hour at room temperature and the reaction solution is then extracted by means of shaking and the use of a 800 ml of water. After the drying with sodium sulphate, the chloroform phase is evaporated in the vacuum at 60° C. bath temperature under the protection by an inert gas. The resulting plastic phosphatide mixture contains approximately 30% of n-oleylphosphatidylethanolamine and approximately 60% of phosphatidylcholine.

EXAMPLE 4

500 grams of a soyaphosphatide fraction, insoluble in alcohol, with a phosphatidylethanolamine content of approximately 33%, as obtained in the form of residue in the course of preparation of the alcohol-soluble fraction described in Example 3, are dissolved in 2500 ml of n-hexane and are treated, after an admixture of 47 ml of triethylamine, with a solution of 52 grams of oleic acid chloride in 75 ml of n-hexane under stirring. The stirring is continued for one hour at room temperature and the precipitated triethylaminehydrochloride is then filtered out and the solution is evaporated in a vacuum at a bath temperature of 60° C. The remaining residue is then extracted under stirring at room temperature, first by the use of 500 ml of acetone and then two times by the use of 250 ml of acetone. From the combined acetone extracts there is then obtained, after removal of the solvent in the vacuum at a bath temperature of 60° C., n-oleylphosphatidylethanolamine in a 70% concentration in the form of a viscous, yellow-brown oil with a phosphatidylcholine content of approximately 25%.

Yield: 240 gram which corresponds to 90% of the theoretical value.

EXAMPLE 5 a. Capsules Filled with a Liquid Compound

Capsules suitable for oral dispensation can be produced in a manner known per se by filling soft gelatin capsules with the n-oleylphosphatidylethanolamines prepared in accordance with the present invention, optionally admixed with Vitamin E (for example, 500 mg of n-oleyphosphatidylethanolamine per capsule).

b. Capsules Filled with a Dry Compound

It is also possible by mixing and grinding n-oleylphosphatidylethanolamine together with Aerosil to produce a pourable powdery material which is suitable for filling hard-gelatin capsules:
n-oleylphosphatidylethanolamine: 250 mg
aerosil: 250 mg.

The capsules manufactured in such a manner can be used for treating the hyperlipemia and the "Athero" sclerosis, with 1 to 2 capsules to be given 2 to 4 times daily.

We claim:

1. N-oleyl derivatives of natural and synthetic phosphatidylethanolamines of the formula:

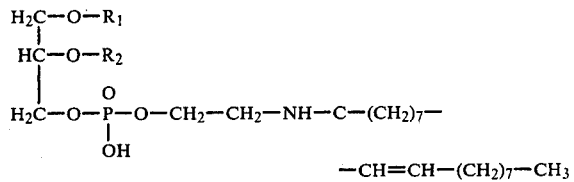

wherein $R_1$ and $R_2$ are saturated, unsaturated, straight-chain or branched aliphatic acids containing 12 to 22 carbon atoms.

2. A pharmaceutical composition having antilipemic and antiarteriosclerotic properties comprising an effective amount of a n-oleyl derivative of a phosphatidylethanolamine having a formula as defined in claim 1.

* * * * *